United States Patent [19]

Collins

[11] Patent Number: 5,206,228

[45] Date of Patent: Apr. 27, 1993

[54] CONTROL OF ARTHROPOD PESTS WITH PHOSPHOROUS ACID AND MONO-ESTERS AND SALTS THEREOF

[75] Inventor: James R. Collins, Cary, N.C.

[73] Assignee: Rhone-Poulenc Ag Company, Research Triangle Park, N.C.

[21] Appl. No.: 784,563

[22] Filed: Oct. 29, 1991

[51] Int. Cl.$^5$ ............................................. A01N 57/18
[52] U.S. Cl. .................................................. 514/141
[58] Field of Search ......................................... 514/141

[56] References Cited

PUBLICATIONS

Worthing et al, The Pesticide Manual, 8th Ed. (1987) p. 484.

*Primary Examiner*—Allen J. Robinson
*Attorney, Agent, or Firm*—James G. Passé

[57] ABSTRACT

The invention relates to pesticidal compositions based on phosphorous acid, monoesters and salts thereof for new methods of use to control arthropod pests on plants or habitats thereof with a compound of a formula (I)

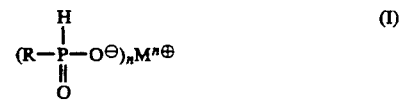

wherein:
  R is an OH or an alkoxy having 1 to 4 carbon atoms;
  M is a hydrogen atom (when R is a hydroxyl radical) or an alkali metal, alkaline earth metal or aluminum cation; and
  n is an integer from 1 to 3.

18 Claims, No Drawings

CONTROL OF ARTHROPOD PESTS WITH PHOSPHOROUS ACID AND MONO-ESTERS AND SALTS THEREOF

BACKGROUND OF THE INVENTION

1. Field of the Invention

The present invention relates to pesticidal compounds and compositions based on phosphorous acid and mono-ester derivatives and especially salts thereof for new and surprisingly unexpected methods of use to control arthropod pests, including insects and arachnids. In particular, it pertains to the application to a locus, especially to plants or the habitat thereof, of said compounds or compositions thereof in agriculture, horticulture, etc. as pesticides, without causing significant injury to the plants and also with good safety to the user and the environment.

2. Description of the Related Art

It has been well known for more than 10 years to use phosphorous acid, its salts and salts of some of its mono-esters, especially aluminum tris-(O-ethyl phosphonate), fosetyl-Al, commonly known as the commercial product ALIETTE®, as an active ingredient effective against plant fungal diseases. It has been more recently discovered that fosetyl-Al is also unexpectedly active against plant bacterial diseases, which differ significantly from fungal diseases in their causes and especially in their difficulty of control.

Fosetyl-Al has the unique feature of being systemically active in both an upward (xylem) and downward (phloem) direction and has thus enabled new strategies to be used in the control of diseases which affect the above ground as well as below ground portions of plants. Thus foliar applications can advantageously combat root diseases, stem/trunk applications can advantageously combat root diseases as well as foliage or fruit diseases, and root, seed or soil applications can advantageously combat diseases of above ground plant portions.

While these compounds, and especially fosetyl-Al, have been well known to combat fungal and bacterial diseases of plants, they have not heretofore been known to be useful to combat other significantly different pest problems. For example, although fosetyl-Al, as an active ingredient in ALIETTE®, has been used in extensive commercial use around the world as a fungicide treatment, it has not been recognized or suggested to have any significant or practical use against arthropod pests, especially insects. In fact, whether against pest (non-beneficial) or beneficial insects and mites, there has been no observation except essentially no or innocuous activity on arthropods.

These uses and activities of phosphorous acid derivatives, especially fosetyl-Al, are described as follows:

- as a fungicide in U.S. Pat. Nos. 4,075,324, 4,139,616 and 4,935,410 and in GB patents 2,137,498 and 2,163,652;
- as a fungicide and bactericide in U.S. Pat. Nos. 4,542,023 and 4,382,928;
- as a bactericide in AU patent A 72530/87, corresponding to EP 249,566;
- as part of a seed treatment fungicide mixture to control fungal diseases and in combination with known insecticides to control thrips and weevils as described in Proc. Brit. Crop Prot. Conf. Pests Dis, Vol. 3, 965-70, 1984 and ibid, Vol. 3, 1093-1100, 1986;
- as one of 7-10 different commercial fungicides for evaluation on the survival and reproduction of fruitfly as described in J. Environ. Sci. Health, B(4), 407-24, 1985 and Acta Oecol., 6(4), 323-330, 1985;
- as a fungicidal seed treatment of cotton seeds for evaluation of fungal disease protection and in combination with various known insecticides for evaluation of effects on millipedes as described in Cot. Fib. Trop., 39(3), 95-97, 1984; and
- as a fungicide for its potentially harmful environmental effects on beneficial arthropods (predator mites and honey bees) as described in Phytoma-Defense Des Cultures, No 346, pages 48–49, 1983.

SUMMARY OF THE INVENTION

The need for safer pesticidal products, especially insecticides, in the environment is highly desirable, especially where they may be used as systemic treatments. This is especially important, for example, where sweet potato whitefly is causing tremendous damage in arid regions and is described as the greatest threat ever to vegetable production. Likewise, practical and cost effective control of thrips and aphids which cause similar and extensive damage requires new and improved measures of control.

The present invention thus relates to pesticidal compositions based on phosphorous acid derivatives for new and surprising methods of use, e.g. for treatment of plants or habitat thereof with said derivatives to control arthropods, including, for example, insects and arachnids (e.g. mites), but especially for control of insects.

In its broadest sense, the present invention provides a method for the control of arthropod pests at a locus which comprises applying to or treating the locus with an effective amount, sufficient to control said arthropods, of an active ingredient compound of a formula (I)

wherein:
R is an OH or an alkoxy having 1 to 4 carbon atoms;
M is a hydrogen atom (when R is a hydroxyl radical) or an alkali metal, alkaline earth metal or aluminum cation; and
n is an integer from 1 to 3.

The compound of formula (I) in its insecticidal use and composition is in association with an agriculturally acceptable carrier or diluent and/or an agriculturally acceptable surface-active agent.

The compounds of formula (I) which are preferred are those wherein R is an alkoxy, having one to four carbon atoms, or a hydroxy, i.e. the compounds are either an O-alkyl phosphonate derivative or a phosphorous acid derivative.

Amongst the preferred compounds of formula (I) are: 1) monosodium or monopotassium phosphonates; 2) disodium or dipotassium phosphonates; or 3) sodium, potassium, calcium or aluminum (O-ethyl phosphonates). Aluminum tris-(O-ethyl phosphonate) is especially preferred.

It is an object of the present invention to provide pesticidal compounds and compositions for new methods of use to control or combat non-beneficial arthropod pests, especially insects, which infest plants or the habitat thereof.

A second objective of the invention is that said new methods to control or combat arthropod pests are made to plants subject to infestation or attack by said pests or are made to plants in need of said control (protection) by virtue of an actual infestation or a subsequent infestation which normally or generally occurs.

Another object of the invention is to provide control of arthropods, especially insects, by direct or indirect means, the latter including systemic action, antifeeding effects, repellent effects, ovicidal effects, etc.

A further object of the invention is to provide simple, cost effective pesticidal compounds which have improved safety to man or his environment during handling, use or application as compared to, for example, typical insecticidal compounds.

DETAILED DESCRIPTION OF THE INVENTION

The compounds of formula (I) of the present invention are readily available or known and can be prepared by procedures such as those reported by Ducret, et al. in U.S. Pat. No. 4,139,616, and Thizy, et al. in U.S. Pat. No. 4,075,324, both of which are incorporated herein by reference.

Representative Compounds of the Invention

The following are some specific examples of phosphorous acid derivative compounds of formula (I), which may alternatively exist in their phosphite forms and which can be advantageously used to control arthropods, especially insects. The compounds may also exist in hydrated forms and also may be mixed salts of more than one metal cation.

phosphorous acid (ortho, $H_3PO_3$)
phosphorous acid mono-sodium salt
phosphorous acid mono-potassium salt
phosphorous acid di-sodium salt
phosphorous acid di-potassium salt
phosphorous acid calcium salt
phosphorous acid aluminum salt
phosphorous acid magnesium salt
phosphorous acid barium salt
sodium O-ethyl phosphonate
potassium O-ethyl phosphonate
calcium bis-(O-ethyl phosphonate)
aluminum tris-(O-ethyl phosphonate)
monosodium (O-methyl phosphonate)
potassium (O-butyl phosphonate)
aluminum tris-(O-isopropyl phosphonate)

Specific Uses Against Arthropod Pests, Especially Insects

The arthropod pest properties of the compounds of formula (I) and the compositions containing them are illustrated in the following examples, wherein the treatment rate of the active ingredient (ai) is expressed in grams (g)/hectare (ha) and the results are expressed in % control vs. the untreated control (UTC).

EXAMPLE 1

Control of thrips and aphids on cotton and peanut plants via in-furrow at planting application under field conditions:

An at planting time application of fosetyl-Al, aluminum tris(O-ethyl phosphonate), was applied to cotton (CT) and peanuts (PT) at six US field and Georgia). The fosetyl-Al was locations in five states (South Carolina, Mississippi, Texas, North Carolina, formulated, as subsequently described, either as a commercially available wettable powder (ALIETTE® 80 WP) or as an ALIETTE®/ROVRAL® 15G, granular, containing about 10% fosetyl-Al and about 5% of the fungicide iprodione [3-(3,5-dichlorophenyl)-N-(1-methylethyl)-2,4-dioxo-1-imidazolidinecarboxamide]. Aldicarb [TEMIK® 15G, 2-methyl-2-methylthio)proionaldehyde O-(methylcarbamoyl)oxime] was used as a commercial standard for comparison.

The applications were made as in-furrow treatments at the time of planting as a 8–10 cm banded spray into the open seed furrow or as a granular treatment (0–8 cm band) placed in the furrow bottom. The treatments, including an untreated control (UTC) were replicated four times in a randomized, complete-block design.

At the specified time, Days After Treatment (DAT), counts of thrips were made on a number of randomly selected plants, usually from the center of each treatment. The counts included immatures (juveniles, nymphs or larval stages) and adults of the following species:

| tobacco thrips (TT) | *Frankliniella fusca* |
| thrips, species (TS) | Frankliniella spp. |
| western flower thrips (WFT) | *Frankliniella tritici* |

Table 1 presents the control of thrips in terms of percent control vs. the UTC at 0%; the level of infestation is shown for each treatment UTC in parentheses as the number of thrips per plant or per 10 plants.

These same treatments also provide some control of cotton aphid (CA, *Aphis gossypii*) where, for example, in the NC test selected cotton plants, artificially infested with cotton aphid at 30 DAT, showed four days later a greater than 50% reduction in the aphid population compared to UTC.

TABLE 1

| PERCENT CONTROL OF THRIPS ON COTTON (CT) AND PEANUTS (PT) | | | | | | | | |
|---|---|---|---|---|---|---|---|---|
| | | CROP: | CT | CT | CT | CT | PT | PT |
| | | PEST: | TT | TS | WFT | TS | TS | TT |
| | | STATE: | SC | MS | TX | NC | GA | GA |
| | | DAT: | 17 | 26 | 30 | 18 | — | 30 |
| IN-FURROW TREATMENT | FORMULATION | RATE, g ai/ha | | | % Control vs. UTC | | | |
| UTC (No. thrips/1 or 10 plants) | | 0 | 0 (5) | 0 (4) | 0 (4) | 0 (12) | 0 (14) | 0 (12) |
| ALIETTE ®/ROVRAL ® | 15G | 448/224 | 4 | 35 | 0 | 84 | 72 | 24 |
| ALIETTE ® | 80WP | 448 | 0 | 53 | 67 | 93 | 62 | 31 |
| ALIETTE ® | 80WP | 224 | 0 | 19 | — | 54 | 56 | 25 |

TABLE 1-continued

| | | | PERCENT CONTROL OF THRIPS ON COTTON (CT) AND PEANUTS (PT) | | | | | |
|---|---|---|---|---|---|---|---|---|
| | | CROP: | CT | CT | CT | CT | PT | PT |
| | | PEST: | TT | TS | WFT | TS | TS | TT |
| | | STATE: | SC | MS | TX | NC | GA | GA |
| | | DAT: | 17 | 26 | 30 | 18 | — | 30 |
| IN-FURROW TREATMENT | FORMU-LATION | RATE, g ai/ha | % Control vs. UTC | | | | | |
| TEMIK ® | 15G | 530 | 87 | 100 | 99 | 100 | 78 | 90 |

EXAMPLE 2

Control of whitefly and cotton leaf perforator on cotton via foliar application under field conditions:

A late season foliar application of fosetyl-Al was applied to cotton in order to evaluate a serious and limiting production factor in cotton, commonly referred to as "sticky cotton" resulting from whitefly (and aphid) infestation, especially occurring in arid regions (Arizona). Evaluation was also made for control of other insect species, especially Lepidoptera. The species evaluated in these tests were as follows:

| whitefly (WF) | Bemesia tabaci |
|---|---|
| corn leaf perforator (CLP) | Bucculatrix thurberiella |

The fosetyl-Al, formulated as the commercially available ALIETTE ® 80 WP was applied in early August as a foliar spray by means of a backpack sprayer to 4 replicated plots arranged in a randomized, complete-block design which included an Untreated Control (UTC) and a commercial standard, aldicarb (TEMIK ® 15G), applied in May as a lay by treatment and/or in June as a side dress treatment. At the specified time, Days After Treatment (DAT), counts of immatures were made on 100 randomly selected leaves. Table 2 presents the control of whitefly and cotton leaf perforator in terms of percent control vs. the UTC at 0%; the level of infestation is shown in parentheses as the average number per leaf.

EXAMPLE 3

Control of pea aphid on beans via foliar application under field conditions:

In a test procedure similar to that of Example 2, a foliar spray application of fosetyl-Al (ALIETTE ® 80 WP) at 4480 g ai/ha provided a visual observation of excellent control (>80%) vs. an untreated plot for pea aphid (Acyrthosiphon pisum) on beans in a North Carolina field trial.

EXAMPLE 4

Greenhouse systemic evaluations—control of cotton aphid and southern armyworm on cotton and greenbug and southern armyworm on sorghum:

The following tests describe some of the typical greenhouse/laboratory procedures for screening of compounds to identify insecticidal activity. The greenhouse screening results described below show that fosetyl-Al, well known for more than 10 years for its fungicidal properties and more recently for unexpected bactericidal properties, has essentially zero activity (at generally normal test levels) or only very low nonsignificant activity or some suppression (at higher exaggerated test levels) on the following insect pests: cotton aphid (CA), *Aphis gossypi*, greenbug (aphid) (GB), *Schizaphis graminum*, and southern armyworm, *Spodoptera eridania*. It was thus quite surprising and unexpected that under field conditions, described above in Examples 1–3, fosetyl-Al provides control, especially via systemic action of several different insect pests, including thrips, aphids, whiteflies and a Lepidopterous species.

A sample of fosetyl-Al technical was used to prepare an aqueous solution in order to deliver 5 ml of a 20 ppm soil concentration dose (and subsequent dilutions 10.0, 5.0, 2.5, 1.25 and 0.625 ppm) as a drench to 6 cm pots containing cotton and sorghum plants. The cotton plants were previously infested with cotton aphids about two days before treatment and greenbug one day before treatment. After holding the plants about three days, the plants were rated for aphid activity. Again at six days, the plants were rated for aphid activity and the cotton aphids and greenbugs were counted and mortality was assessed. Portions of the cotton and sorghum foliage were excised, placed in separate plastic containers, and infested with second instar larvae of southern armyworms. The potted plants were dipped in sulfotepp to kill the remaining aphids and returned to the greenhouse for regrowth. Thirteen days after treatment the remaining foliage was excised and fed to southern armyworm. Mortality was assessed five days after infestation.

TABLE 2

| PERCENT CONTROL OF WHITEFLY (WF) AND COTTON LEAF PERFERATOR (CLP) ON COTTON IN ARIZONA | | | | | | | |
|---|---|---|---|---|---|---|---|
| | | | PEST: | WF | WF | CLP | WF |
| | | | LOCATION: | Yuma | Yuma | Yuma | Coolidge |
| | | | DAT: | 3 | 11 | 3 | 3 |
| TREATMENT | FORMU-LATION | | RATE, g ai/ha | % Control vs. UTC | | | |
| UTC | | | 0 | 0 (6.4) | 0 (10.0) | 0 (1.2) | 0 (0.32) |
| ALIETTE ® | 80WP | (8/91 foliar spray) | 4480 | 42 | 39 | 42 | 78 |
| TEMIK ® | 15G | (5/91 lay by) | 2520 | 16 | 20 | 58 | 56 |
| TEMIK ® | 15G | (6/91 sidedress) | 2520 | 17 | 37 | 100 | 75 |
| TEMIK ® | 15G | (5/91 lay by and) (6/91 sidedress) | 1680 1680 | 34 | 33 | 100 84 | |

In these tests, fosetyl-Al gave zero % control of both aphid species on cotton at soil concentrations of 10 ppm or less and some suppression (<50%) of cotton aphid larvae and adults at 20 ppm. Control of southern armyworm was: 0% on sorghum at 20 ppm or less; 0% on cotton at 0.625 ppm; and only a low level of about 20% on cotton at the higher doses of 2.5 and 10 ppm.

GENERAL METHODS, COMPOSITIONS AND USE

As is evident from the foregoing pesticidal uses, the present invention provides unexpected pesticidally active compounds and methods of use of said compounds for the control of a number of arthropodal pest species especially which includes insects and more particularly thrips and aphids. The compounds thus are advantageously employed in practical uses, for example, in agricultural or horticultural crops, forestry, ornamentals and turf.

A feature of the present invention therefore provides a method of control of arthropod pests at a locus which comprises the treatment of the locus (e.g., by application or administration) with an effective amount of a compound of general formula (I). The locus includes, for example, the pest itself or habitat thereof for pests which infest plants and thus include, for example, the medium in which the plants grows (e.g., soil or water), or the plant itself including foliage, trunk, roots and seed.

These compounds may be useful in the control via foliar application or systemic action of arthropods, especially some insects or mites, which feed on the above ground portions of plants. Control of foliar pests may additionally be provided by application to the plant roots or plant seeds with subsequent systemic translocation to the above ground portions of the plants.

As indicated above, the compounds of the invention are advantageous used to control arthropod pests, especially insects. The term control is meant to include, for example, killing, inhibiting, combatting, suppressing, repelling or detering the arthropod pest or alternatively, by these means or others, protecting a plant in order to prevent damage to the plant caused by the arthropod pest. These may more specifically include, but are not limited to: 1) repelling/influencing/discouraging the pests not to lay eggs on plants subjected to or treated with compounds of the invention; 2) action, direct or indirect, as an ovicidal treatment to inhibit egg development; 3) action, direct or indirect, as a pest feeding inhibitor to deter insect feeding due to the presence of a compound of the invention or the presence of other compounds or circumstances on or within a plant induced by the compound of the invention; and 4) affecting the physiology of a plant by, for example, dropping the internal or external pH of the plant.

Examples of arthropod pests which may be controlled by compounds of the invention include, for example:

In the class Insecta:
Homoptera Order (piercing-sucking), e.g.,

| | |
|---|---|
| Cercopidae family | spittlebug |
| Membracidae family | treehopper |
| Cicadellidae family | leafhopper |
| Aphididae family | aphids |
| Aleyrodidae family | whiteflies |
| Coccidae family | scales and mealybugs |
| Psyllidae family | psyllids |
| Fulgoridae family | planthoppers |

Thysanoptera Order (piercing-sucking), e.g.,

| | |
|---|---|
| Thripidae family | thrips |
| Phaethripidae family | thrips |

Lepidoptera Order (chewing), e.g.,

| | |
|---|---|
| Noctuidae family | caterpillars, moths |
| Lyonetudae family | caterpillars, moths |

In the class Acari: (piercing-sucking), e.g.,

| | |
|---|---|
| Tetranychidae family | mites |
| Eriophyidae family | mites |
| Tenuipalpidae family | mites |

Some more specific individual arthropod pests, especially insects, which may be controlled are:

| | |
|---|---|
| tobacco thrips | *Frankliniella fusa* |
| flower thrips | *Frankliniella tritici* |
| soybean thrips | *Sericothrips variabilis* |
| onion thrips | *Thrips tabaci* |
| thrips palmi | *Thrips palmi* |
| citrus thrips | *Scirtothrips titri* |
| grape thrips | *Drepanothrips reuteri* |
| western flower thrips | *Frankliniella occidentalis* |
| greenhouse thrips | *Heliothrips haemorrhoidalis* |
| iris thrips | *Iridothrips iridis* |
| gladiolus thrips | *Thrips simplex* |
| grain thrips | *Limothrips cerealium* |
| pea thrips | *Kakothrips robustus* |
| plague thrips | *Thrips imaginis* |
| cotton aphids | *Aphis gossypii* |
| grapevine aphid | *Aphis illinoisensis* |
| greenbut | *Schizaphis graminum* |
| pea aphid | *Acyrthosiphon pisum* |
| Russin wheat aphid | *Diuraphis noxia* |
| corn leaf aphid | *Rhopalosiphum maidis* |
| green peach aphid | *Myzus persicae* |
| potato aphid | *Macrosiphum euphorbae* |
| melon aphid | *Aphis gossypii* |
| ornate aphid | *Myzus ornatus* |
| rose aphid | *Macrosiphum rosae* |
| tulip bulb aphid | *Dysaphis tulipae* |
| chrysanthemum aphid | *Macrosiphoniella sanborni* |
| flea hopper | — |
| greenhouse whitefly | *Trialeurodes vaporariorum* |
| sweet potato whitefly | *Bemisia tabaci* |
| citrus whitefly | *Dialeurodes citri* |
| citrus blackfly | *Aleurocanthus woglumi* |
| whitefly | *Bemesia tabaci* (Poinsetta strain) |
| whitefly | *Bemesia tabaci* (Cotton strain) |
| whitefly | *Trialeurodes abutilonea* |
| whitefly | *Trialeurodes pergandei* |
| woolly whitefly | *Aleurothrixus floccosus* |
| cloudy-winged whitefly | *Dialeurodes citrifolii* |
| grape whitefly | *Trialeurodes vitiata* |
| azalea whitefly | *Pealius azaleae* |
| citrus mealybug | *Planococcus citri* |
| Mexican mealybug | *Phenacoccus gossypii* |
| grape mealybut | *Pseudococcus maritimus* |
| cottony-cushion scale | *icerya purchasi* |
| black scale | *Saissetia oleae* |
| California red scale | *Aonidiella aurantii* |
| Chaff scale | *Parlatoria pergandii* |
| purple scale | *Lepidosaphes beckii* |
| glover scale | *Lepidosaphes gloveri* |
| Florida red scale | *Chrysomphalus aonidum* |
| brown soft scale | *Coccus hesperidum* |
| San Jose scale | *Quadrapidiotus perniciosus* |
| white peach scale | *Pseudaulacaspis pentagona* |
| terrapin scale | *Lecanium migrofasciatum* |
| European fruit lecanium | *Lecanium corni* |
| oleander scale | *Aspidiotus nerii* |
| boisduval scale | *Diaspis boisduvalii* |
| phylloxera | *Phylloxera vitifoliae* |
| pecan spittlebug | *Clastoptra achantinia* |
| pecan leaf phylloxera | *Phylloxera notabilis* |
| pecan phylloxera | *Phylloxera devastatrix* |
| cottonleaf perforator | *Bucculatrix thurberiella* |
| southern armyworm | *Spodoptera eridania* |

| | |
|---|---|
| twospotted spider mite | *Tetranychus urticae* |

The invention, as previously described, provides methods of control of pests via application or administration of an effective amount of compounds of formula (I) at a locus which comprises treatment of the locus.

In practical use for the control of arthropods, especially insects or mites, a method, for example, comprises applying to the plants or to the medium in which they grow an effective amount of a compound of the invention. For such a method, the active compound is generally applied to the locus in which the arthropod pest infestation (actual or subsequently occurring) is to be controlled at an effective amount of the compound or composition containing said compound sufficient to control the pest infestation.

As described herein, the compounds and their compositions can be applied in effective amounts by a number of different techniques readily known to one skilled in the art. These include, for example: as a foliar or soil application to field crops at about 0.1 to about 15 kg ai/ha, preferably about 1 to about 5 kg ai/ha; as a tree trunk injectable solution of about 1 to about 25% ai to avocados and citrus to provide about 0.1 to about 10 g ai/meter of canopy diameter, preferably about 0.5 to about 2 g ai/meter of canopy diameter, which for a full grown tree is about 2 to about 8 g ai/tree; as a tree trunk paint to citrus, stone and pome fruit of about 1 to about 25% ai in water to provide about 1 to about 100 g ai/tree, preferably about 5-50 g ai/tree; as a root dip to e.g. strawberry and citrus seedlings as a liquid solution or suspension containing about 1 to about 120 g ai/l, preferably about 2 to about 30 g ai/l; and as a seed treatment of about 0.2 to about 30.0 g ai/kg of seed, preferably about 0.5 to about 5.0 g ai/kg of seed and may be higher or lower than these ranges depending on factors such as type and size of seed and pest to be controlled. Under ideal conditions, depending on the pest to be controlled, the lower rate may offer adequate protection. On the other hand, adverse weather conditions, resistance of the pest or other factors may require that the active ingredient be used at the higher rates. The optimum rate depends usually upon a number of factors, for example, the type of pest being controlled, the type or the growth stage of the infested plant, the row spacing or also the method of application. The actual compositions employed and their effective rate of application will be selected to achieve the desired effect(s) by the user or other person skilled in the art.

When a pest is soil-borne, the active compound generally in a formulated composition, is distributed evenly over the area to be treated (i.e., for example broadcast or band treatment) in any convenient manner. Application may be made, if desired, to the field or crop-growing area generally or in close proximity to the seed or plant to be protected from attack. The active component can be washed into the soil by spraying with water over the area or can be left to the natural action of rainfall. During or after application, the formulated compound can, if desired, be distributed mechanically in the soil, for example by ploughing, disking, or use of drag chains. Application can be prior to planting, at planting, after planting but before sprouting has taken place, or after sprouting. Additionally, a method of control may also comprise treatment of the seed prior to planting with subsequent control effected after planting the seed.

Methods of control of pests also consist of application to or treatment of the foliage of plants to control arthropods, especially insects or mites attacking the aerial parts of the plants. In addition, methods of control of pests by the invention compounds are provided to control pests which feed on parts of the plant remote from the point of application, e.g., leaf feeding insects which are controlled via systemic action of the active compound when applied for example to the roots of a plant or to the plant seed prior to planting. Furthermore, the compounds of the invention may reduce attacks on a plant by means of antifeeding or repellent effects.

The compounds of the invention and methods of control of pests therewith are of particular value in the protection of field, forage, plantation, glasshouse, orchard or vineyard crops, ornamentals, or plantation or forest trees, or turf, for example: cereals (such as oats, barley, wheat or rice); vegetables (such as beans, cole crops, curcurbits, lettuce, spinach, celery, onions, tomatoes or asparagus); field crops (such as cotton, tobacco, maize, sorghum, hops, peanuts or soybeans); small fruits (such as caneberries or strawberries); plantations (such as coffee or cocoa); orchards or groves (such as of stone (peaches, almonds or nectarines), pome (apples) or pit fruit, citrus (oranges, lemons, grapefruit), pecan or avocado trees; grape vineyards; ornamental plants; flowers or vegetables or shrubs under glass or in gardens or parks; forest trees (both deciduous and evergreen) in forests, plantations or nurseries; or turf.

The compositions hereinafter described for application to growing crops or crop growing loci may be employed using suitable means of applying the compounds of the invention which include: to growing crops: as foliar sprays, dusts, granules, fogs or foams or also as suspensions of finely divided or encapsulated compositions; as soil or root treatments by liquid drenches, dusts, granules, smokes or foams; to seeds of crops via application as seed dressings by liquid slurries or dusts; or as a trunk injection or paint by an appropriate liquid or paste formulation.

In practice, the compounds of the invention most frequently form parts of compositions. These compositions can be employed to control: arthropods, especially insects or mites. The compositions may be of any type known in the art suitable for application to the desired pest or habitat thereof. These compositions contain at least one compound of the invention, such as described earlier, as the active ingredient in combination or association with one or more other compatible components which are for example, solid or liquid carriers or diluents, adjuvants, surface-active-agents, or the like appropriate for the intended use and which are agronomically acceptable. These arthropod pest compositions, which may be prepared by any manner known in the art, likewise form a part of this invention.

These compositions may also contain other kinds of ingredients such as protective colloids, adhesives, thickeners, thixotropic agents, penetrating agents, spray oils (especially for acaridical use), stabilizers, preservative agents (especially mold preservatives), sequestering agents, or the like, as well as other known active ingredients with pesticidal properties (particularly insecticidal, miticidal, nematicidal, or fungicidal) or with properties regulating the growth of plants. More generally, the compounds employed in the invention may be combined with all the solid or liquid additives corresponding to the usual techniques of formulation.

Compositions, suitable for applications in agriculture, horticulture, or the like include formulations suitable for use as, for example, liquid sprays, dusts, granules, fogs, foams, emulsions, or the like.

The effective use doses of the compounds employed in the invention can vary within wide limits, particularly depending on the nature of the pest to be eliminated or degree of infestation, for example, of crops with these pests. In general, the compositions (concentrated or diluted ready to use) according to the invention usually contain about 0.001 to about 95% (by weight) of one or more active ingredients according to the invention, about 1 to about 95% of one or more solid or liquid carriers and, optionally, about 0.1 to about 50% of one or more other compatible components, such as surface-active agents or the like.

In the present account, the term "carrier" denotes an organic or inorganic ingredient, natural or synthetic, with which the active ingredient is combined to facilitate its application, for example, to the plant, to seeds or to the soil. This carrier is therefore generally inert and it must be acceptable (for example, agronomically acceptable, particularly to the treated plant).

The carrier may be a solid, for example, clays, natural or synthetic silicates, silica, resins, waxes, solid fertilizers (for example ammonium salts), ground natural minerals, such as kaolins, clays, talc, chalk, quartz, attapulgite, montmorillonite, bentonite or diatomaceous earth, or ground synthetic minerals, such as silica, alumina, or silicates especially aluminium or magnesium silicates. As solid carriers for granules the following are suitable: crushed or fractionated natural rocks such as calcite, marble, pumice, sepiolite and dolomite; synthetic granules of inorganic or organic meals; granules of organic material such as sawdust, coconut shells, corn cobs, corn husks or tobacco stalks; kieselguhr, tricalcium phosphate, powdered cork, or absorbent carbon black; water soluble polymers, resins, waxes; or solid fertilizers. Such solid compositions may, if desired, contain one or more compatible wetting, dispersing, emulsifying or coloring agents which, when solid, may also serve as a diluent.

The carrier may also be liquid, for example: water; alcohols, particularly butanol or glycol, as well as their ethers or esters, particularly methylglycol acetate; ketones, particularly acetone, cyclohexanone, methylethyl ketone, methylisobutylketone, or isophorone; petroleum fractions such as paraffinic or aromatic hydrocarbons, particularly xylenes or alkyl naphthalenes; mineral or vegetable oils; aliphatic chlorinated hydrocarbons, particularly trichloroethane or methylene chloride; aromatic chlorinated hydrocarbons, particularly chlorobenzenes; watersoluble or strongly polar solvents such as dimethylformamide, dimethyl sulphoxide, or N-methylpyrrolidone; liquefied gases; or the like or a mixture thereof.

The surface-active agent may be an emulsifying agent, dispersing agent or wetting agent of the ionic or non-ionic type or a mixture of such surface-active agents. Amongst these are e.g., salts of polyacrylic acids, salts of lignosulphonic acids, salts of phenolsulphonic or naphthalenesulphonic acids, polycondensates of ethylene oxide with fatty alcohols or fatty acids or fatty esters or fatty amines, substituted phenols (particularly alkylphenols or arylphenols), salts of sulphosuccinic acid esters, taurine derivatives (particularly alkyltaurates), phosphoric esters of alcohols or of polycondensates of ethylene oxide with phenols, esters of fatty acids with polyols, or sulphate, sulphonate or phosphate functional derivatives of the above compounds. The presence of at least one surface-active agent is generally essential when the active ingredient and/or the inert carrier are only slightly water soluble or are not water soluble and the carrier agent of the composition for application is water.

Compositions of the invention may further contain other additives such as adhesives or colorants. Adhesives such as carboxymethylcellulose or natural or synthetic polymers in the form of powders, granules or lattices, such as arabic gum, polyyinyl alcohol or polyvinyl acetate, natural phospholipids, such as cephalins or lecithins, or synthetic phospholipids can be used in the formulations. It is possible to use colorants such as inorganic pigments, for example: iron oxides, titanium oxides or Prussian Blue; organic dyestuffs, such as alizarin dyestuffs, azo dyestuffs or metal phthalocyanine dyestuffs; or trace nutrients such as salts of iron, manganese, boron, copper, cobalt, molybdenum or zinc, Compositions containing compounds of general formula (I) which may be applied to control arthropod pests, may also contain synergists (e.g. piperonyl butoxide or sesamex), stabilizing substances, other insecticides, acaricides, plant nematicides, fungicides, e.g. benomyl and iprodione, bactericides, arthropod attractants or repellents or pheromones, deodorants, flavoring agents, dyes, or auxiliary therapeutic agents, e.g. trace elements. These may be designed to improve potency, persistence, safety, uptake where desired, spectrum of pests controlled or to enable the composition to perform other useful functions in the same animal or area treated.

Examples of other pesticidally-active compounds which may be included in, or used in conjunction with the compositions of the present invention are: acephate, chlorpyrifos, demeton-S-methyl, disulfoton, ethoprofos, fenitrothion, fenamiphos, fonofos, iprodione, isazophos, isofenphos, malathion, monocrotophos, parathion, phorate, phosalone, pirimiphos-methyl, terbufos, triazophos, cyfluthrin, cypermethrin, deltamethrin, fenpropathrin, fenvalerate, permethrin, tefluthrin, aldicarb, carbosulfan, methomyl, oxamyl, pirimicarb, bendiocarb, teflubenzuron, dicofol, endosulfan, lindane, benzoximate, cartap, cyhexatin, tetradifon, avermectins, ivermectins, milbemycins, thiophanate, trichlorfon, dichlorvos, diaveridine or dimetriadazole.

Regarding the use of compounds of the invention and in particular fosetyl-Al, it has been found that some compositions and uses thereof advantageously contain stabilizing agents which can include, for example: a water soluble zinc or calcium salt of a weak acid (mineral or organic) as described by Barlet in GB patent 2,163,652 and 2,137,498, especially useful for injection into the trunks of crop trees or shrubs; or a water soluble salt of a strong base (mineral or organic) and a weak mineral or organic acid as described by Barlet for sprays, dips or injection in U.S. Pat. No. 4,935,410, incorporated herein by reference.

For their agricultural application, the compounds of the formula(I) are therefore generally in the form of compositions, which are in various solid or liquid forms.

Solid forms of compositions which can be used are dusting powders (with a content of the compound of formula(I) ranging up to 80%), wettable powders or granules (including water dispersible granules), particularly those obtained by extrusion, compacting, impregnation of a granular carrier, or granulation starting from a powder (the content of the compound of formula(I) in these wettable powders or granules being between about 0.5 and about 95%). Solid homogenous or heterogenous compositions containing one or more compounds of general formula(I) for example granules, pellets, briquettes or capsules, may be used to treat standing or running water over a period of time. A similar effect may be achieved using trickle or intermittent feeds of water dispersible concentrates as described herein.

Liquid compositions, for example, include aqueous or non-aqueous solutions or suspensions (such as emulsifiable concentrates, emulsions, flowables, dispersions, or solutions) or aerosols. Liquid compositions also include, in particular, emulsifiable concentrates, dispersions, emulsions, flowables, aerosols, wettable powders (or powder for spraying), dry flowables or pastes as forms of compositions which are liquid or intended to form liquid compositions when applied, for example as aqueous sprays (including low and ultra-low volume) or as fogs or aerosols.

Liquid compositions, for example, in the form of emulsifiable or soluble concentrates most frequently comprise about 5 to about 90% by weight of the active ingredient, while the emulsions or solutions which are ready for application contain, in their case, about 0.01 to about 20% of the active ingredient. Besides the solvent, the emulsifiable or soluble concentrates may contain, when required, about 2 to about 50% of suitable additives, such as stabilizers, surface-active agents, penetrating agents, corrosion inhibitors, colorants or adhesives. Emulsions of any required concentration, which are particularly suitable for application, for example, to plants, may be obtained from these concentrates by dilution with water. These compositions are included within the scope of the compositions which may be employed in the present invention. The emulsions may be in the form of water-in-oil or oil-in-water type and they may have a thick consistency.

All these aqueous dispersions or emulsions or spraying mixtures can be applied, for example, to crops by any suitable means, chiefly by spraying, at rates which are generally of the order of about 100 to about 1,200 liters of spraying mixture per hectare, but may be higher or lower (e.g. low or ultra-low volume) depending upon the need or application technique. The compounds or compositions according to the invention are conveniently applied to vegetation and in particular to roots, seeds, stems or leaves having pests to be eliminated. Another method of application of the compounds or compositions according to the invention is by chemigation, that is to say, the addition of a formulation containing the active ingredient to irrigation water. This irrigation may be sprinkler irrigation for foliar pesticides or it can be ground irrigation or underground irrigation for soil or for systemic pesticides.

The concentrated suspensions, which can be applied by spraying, are prepared so as to produce a stable fluid product which does not settle (fine grinding) and usually contain from about 10 to about 75% by weight of active ingredient, from about 0.5 to about 30% of surface-active agents, from about 0.1 to about 10% of thixotropic agents, from about 0 to about 30% of suitable additives, such as anti-foaming agents, corrosion inhibitors, stabilizers, penetrating agents, adhesives and, as the carrier, water or an organic liquid in which the active ingredient is poorly soluble or insoluble. Some organic solids or inorganic salts may be dissolved in the carrier to help prevent settling or as antifreezes for water.

The wettable powers (or powder for spraying) are usually prepared so that they contain from about 10 to about 95% by weight of active ingredient, from about 20 to about 90% of a solid carrier, from about 0 to about 5% of a wetting agent, from about 3 to about 10% of a dispersing agent and, when necessary, from about 0 to about 10% of one or more stabilizers and/or other additives, such as penetrating agents, adhesives, anti-caking agents, colorants, or the like. To obtain these wettable powders, the active ingredient(s) is(are) thoroughly mixed in a suitable blender with additional substances which may be impregnated on the porous filler and is(are) ground using a mill or other suitable grinder. This produces wettable powders, the wettability and the suspendability of which are advantageous. They may be suspended in water to give any desired concentration and this suspension can be employed very advantageously in particular for application to plant foliage.

The "water dispersible granules (WG)" (granules which are readily dispersible in water) have compositions which are substantially close to that of the wettable powders. They may be prepared by granulation of formulations described for the wettable powders, either by a wet route (contacting finely divided active ingredient with the inert filler and a little water, e.g. 1 to 20% by weight, or with an aqueous solution of a dispersing agent or binder, followed by drying and screening), or by a dry route (compacting followed by grinding and screening).

Specific Composition Examples

The following composition Examples 5-15 made by well known techniques or those described herein, illustrate compositions for use against arthropod pests, especially mites or insects, which comprise, as active ingredient, compounds of general formula (I), such as those described above. A composition as described in Example 5, 6 and 13-15 can be diluted in water to give a sprayable composition at concentrations suitable for use in the field. The examples describe the ingredients in terms of their common or trade names, chemical names, and weight percent in the composition.

EXAMPLE 5

An ALIETTE ® 80WP (wettable powder) was prepared by standard procedures containing the following ingredients in Wt. %:

| | | |
|---|---|---|
| fosetyl-Al, tech. | aluminum tris-(O-ethyl phosphonate) | 84.2 |
| T-DET N-40 | ethoxylated nonyl phenol (40 moles ethylene oxide, E.O.) | 3.0 |
| Ronex 30 | polyoxyethylene (12 moles E.O.) tridecyl ether | 1.5 |
| Surfynol 104S | 50:50 blend of hydrated silica and 2,4,7,9-tetramethyl-5-decyn-4,7-diol | 2.0 |
| Polyfon F | lignosulfonate, sodium salt | 3.0 |
| Hi Sil 233 | hydrated silica | 3.0 |
| Barden Ag-1 | Kaolinite clay | 3.3 |

EXAMPLE 6

An 80 WDG (water dispersible granule) is prepared as follows containing the following ingredients in Wt. %:

| | | |
|---|---|---|
| fosetyl-Al, tech. | aluminum tris-(O-ethyl phosphonate) | 82.5 |
| Igepal C0890 | ethoxylated nonyl phenol (40 moles ethylene oxide) | 3.0 |
| Igepa; CO660 | ethoxylated nonyl phenol (10 moles ethylene oxide) | 2.0 |
| — | calciumacetate, 0.5 $H_2O$ | 5.0 |
| Rhodosil 454 | polydimethyl siloxane oil plus inert filler | 0.5 |
| Volclay HPM-20 | bentonite clay | 4.0 |
| Morwet D-425 | sodiumsalt of sulfonated naphthalene-formaldehyde condensate | 3.0 |

EXAMPLE 7

An ALIETTE® (10%)/Rovral (5%) 15G (granular) was prepared with the following ingredients in Wt. %:

| | | |
|---|---|---|
| ALIETTE® 80 WP | as in EXAMPLE 5 | 12.6 |
| ROVRAL® 50 WP | | 10.2 |
| Iprodione, tech | 3-(3,5-dichlorophenyl)-N-(1-methylethyl)-2,4-dioxo-1-imidazolidinecarboxamide | 53.16 |
| Reax 45L | lignosulfonate sodium salt | 6.0 |
| Attaclay | attapulfite clay | 40.84 |
| gypsum | calcium sulfate | 67.2 |
| Norlig 11 dg | lignosulfonate calcium salt | 10.0 |

EXAMPLES 8–12

Other 15G (granular) compositions were prepared with the following ingredients in Wt. %:

EXAMPLE 8

| | | |
|---|---|---|
| fosetyl-Al, tech. | aluminum tris-(O-ethyl phosphonate) | 10.8 |
| iprodione, tech. | 3-(3,5-dichlorophenyl)-N-(1-methylethyl)-2,4-dioxo-1-imidazolidinecarboxamide | 5.4 |
| Norlig 11 dg | lignosulfonate calcium salt | 10.0 |
| gypsum | calcium sulfate | 73.8 |

EXAMAPLE 9

| | | |
|---|---|---|
| fosetyl-Al, tech. | aluminum tris-(O-ethyl phosphonate) | 10.6 |
| iprodione, tech. | 3-(3,5-dichlorophenyl)-N-(1-methylethyl)-2,4-dioxo-1-imidazolidinecarboxamide | 5.3 |
| Norlig 11 dg | lignosulfonate calcium salt | 12.0 |
| gypsum | calcium sulfate | 57.1 |
| hardwood flour | — | 15.0 |

EXAMPLE 10

| | | |
|---|---|---|
| fosetyl-Al, tech. | aluminum tris-(O-ethyl phosphonate) | 10.6 |
| iprodione, tech. | 3-(3,5-dichlorophenyl)-N-(1-methylethyl)-2,4-dioxo-1-imidazolidinecarboxamide | 5.3 |
| Norlig 11 dg | lignosulfonate calcium salt | 15.0 |
| gypsum | calcium sulfate | 54.1 |
| walnut shell flour | — | 15.0 |

EXAMPLE 11

| | | |
|---|---|---|
| fosetyl-Al, tech. | aluminum tris-(O-ethyl phosphonate) | 10.8 |
| iprodione, tech. | 3-(3,5-dichlorophenyl)-N-(1-methylethyl)-2,4-dioxo-1-imidazolidinecarboxamide | 5.4 |
| corn meal | — | 43.8 |
| whole wheat flour | — | 40.0 |

EXAMPLE 12

| | | |
|---|---|---|
| fosetyl-Al, tech. | aluminum tris-(O-ethyl phosphonate) | 10.8 |
| iprodione, tech. | 3-(3,5-dichlorophenyl)-N-(1-methylethyl)-2,4-dioxo-1-imidazolidinecarboxamide | 5.4 |
| Norlig 11 dg | lignosulfonate calcium salt | 10.0 |
| gypsum | calcium sulfate | 23.8 |
| whole wheat flour | — | 50.0 |

Liquid formulations, including suspensions may also be prepared as described below.

EXAMPLE 13

A stabilized water based dispersion was prepared with the following ingredients in Wt. %:

| | | |
|---|---|---|
| fosetyl-Al, tech. | aluminum tris-(O-ethyl phosphonate) | 52.0 |
| — | ethoxylated nonyl phenol (40 moles E.O.) | 3.5 |
| — | ethoxylated nonyl phenol (10 moles E.O.) | 0.6 |
| — | sodium salt of sulfonated lignin | 3.0 |
| — | polydimethyl siloxane | 0.2 |
| — | sodium acetate | 2.5 |
| — | hydrated silicon dioxide | 0.6 |
| — | sodium benzoate* | 0.6 |
| — | sodium bentonite clay | 1.5 |
| — | xanthum gum | 0.2 |
| — | deionized water | 35.3 |

*In the above or other aqueous compositions, a stabilizer, e.g. of a metallic salt is normally required. These include, e.g. calciumor potassium acetate, sodium or calcium propionate, ethylene diamine tetraacetic acid and salts, sodium benzoate, etc.

EXAMPLE 14

The following stabilized concentrated aqueous suspension was prepared with ingredients in Wt. %:

| | | |
|---|---|---|
| fosetyl-Al, tech. | aluminum tris-(O-ethyl phosphonate) | 52.0 |
| — | ethoxylated nonyl phenol (40 moles E.O.) | 3.0 |
| — | ethoxylated nonyl phenol (10 moles E.O.) | 1.2 |
| — | sodium salt of sulfonated naphthalene-formaldehyde condensate | 1.9 |
| — | clacium acetate | 3.1 |
| — | sodium bentonite clay | 2.0 |
| — | polydimethyl siloxane | 0.3 |
| — | hydrated silicon dioxide | 0.6 |
| — | xanthan gum | 0.2 |
| — | deionized water | 35.7 |

EXAMPLE 15

The following stabilized oil based emulsifiable dispersion was obtained with ingredients in Wt. %:

| | | |
|---|---|---|
| fosetyl-Al, tech. | aluminum tris-(O-ethyl phosphonate) | 31.90 |
| Orchex 796 | mixed parafinic/cycloparafinic oil | 45.23 |
| Aleolec S | soya lecithin | 5.68 |
| Morwet IP | isopropyl naphthalene sulfonae | 2.18 |
| Bentone 38 | modified Bentonite clay | 1.31 |
| — | methanol | 0.42 |

| — | deionized water | 0.02 |
| Aerosol OTS | sodium dioctyl sulfosuccinate (in mineral spirits) | 4.69 |
| Tergitol 0683 | ethoxylated and propoxylaed nonyl phenol | 4.68 |
| Pluronic L63 | ethylene oxide/propylene oxide co-polymer | 0.94 |
| Ganex V216 | alkylated polyvinyl pyrrolidone | 1.54 |
| Versene | ethylene diamine tetraacetic acid | 0.94 |
| DAP | diammonium phosphate | 0.47 |

Alternatively in the above example, DAP can be replaced with a stabilizing agent such as described in Example 13. Also alternate suspending agents in place of Bentonite clay are polyacrylic acid polymers and gelling agents such as sodium benzoate plus sodium lauryl sulfate.

What is claimed is:

1. A method of use to control arthropod pests which comprises applying to said pests or an infested locus thereof an effective amount, sufficient to control or combat said arthropods, of an active ingredient compound of a formula (I)

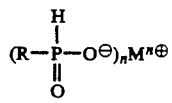

wherein:
R is an OH or an alkoxy having 1 to 4 carbon atoms;
M is a hydrogen atom (when R is a hydroxyl radical) or an alkali metal, alkaline earth metal or aluminum cation; and
n is an integer from 1 to 3.

2. The method of claim 1, in which the locus is a plant, plant part or habitat thereof.

3. The method of claim 2, in which the arthropod pests are insect pests of the Homoptera, Thysanoptera or Lepidoptera order or mite pests of the class Acari.

4. The method of claim 3, in which the insect pests are aphids in the family Aphididae, whiteflies in the family Aleyrodidae, thrips in the family Thripidae or Phaethripidae, or caterpillars or moths in the family Noctuidae or Lyonetudae and the mite pests are in the family Tetranychidae, Eriophyidae or Tenuipalpidae.

5. The method of claim 4, in which the insect pests are whiteflies in the family Aleyrodidae or thrips in the family Thripidae or Phaethripidae.

6. The method of claim 4, wherein the compound is applied to the plant or plant parts or habitat thereof, at an effective amount: as a foliar or soil treatment at about 0.1 to about 15 kg ai/ha; as a tree trunk injectable solution at about 0.1 to about 10 g ai/meter of canopy diameter; as a tree trunk paint at about 1 to about 100 g ai/tree; as a root dip to seedlings with a liquid solution or suspension of about 1 to about 120 g ai/l; or as a seed treatment at about 0.2 to about 30 g ai/kg of seed.

7. The method of claim 6, wherein the effective amount of the compound is: about 1 to about 5 kg/ha for foliar or soil treatment; about 0.5 to about 2 g ai/meter of canopy diameter for tree trunk injection; about 5 to about 50 g ai/tree for a tree trunk paint; about 2 to about 30 g ai/l for a root dip solution or suspension; or about 0.5 to about 5.0 g ai/kg of seed for seed treatment.

8. The method of claim 2, whereby the control or combatting of arthropod pests on plants is obtained by direct or indirect contact action, systemic action, antifeeding effects, repellent effects, ovicidal effects or plant physiology effects.

9. The method of claim 7, wherein the plants are: field crops; forage crops; plantation crops; glasshouse crops; orchard or vineyard crops; ornamentals; plantation or forest trees; vegetable crops; or turf.

10. The method of claim 9, wherein the plants are: oats, barley, wheat or rice cereals; cotton, tobacco, maize, sorghum, hops, peanuts or soybean field crops; caneberry or strawberry small fruits; coffee or cocoa plantations; peaches, almonds or nectarine stone fruits; apple pome fruits; orange, lemon or grapefruit citrus; pecan or avocado trees; grape vineyards; flowers or shrubs or ornamentals; curcurbit, cole crop, lettuce, spinach, celery, onions, tomato or asparagus vegetables; or turf.

11. The method of claim 1, wherein for the compound of formula (I), R is OH or $C_2H_5O$ and M is H, Na, K, Ca or Al.

12. The method of claim 11, wherein the compound is phosphorous acid in which R is OH, M is H and n is 1.

13. The method of claim 11, wherein the compound is aluminum tris-(O-ethyl phosphonate), in which R is $C_2H_5O$, M is Al and n is 3.

14. The method of claim 13, which further comprises a combination with an effective amount, sufficient to control fungal species of a fungicidal compound, 3-(3,5-dichlorophenyl)-N-(1-methylethyl)-2,4-dioxo-1-imidazoleidinecarboxamide.

15. The method of claim 10, wherein for the compound of formula (I), R is OH or $C_2H_5O$ and M is H, Na, K, Ca or Al.

16. The method of claim 15, wherein the compound is phosphorous acid in which R is OH, M is H and n is 1.

17. The method of claim 15, wherein the compound is aluminum tris-(O-ethyl phosphonate), in which R is $C_2H_5O$, M is Al and n is 3.

18. The method of claim 17, which further comprises a combination with an effective amount, sufficient to control fungal species of a fungicidal compound, 3-(3,5-dichlorophenyl)-N-(1-methylethyl)-2,4-dioxo-1-imidazoleidinecarboxamide.

* * * * *